United States Patent
Halden et al.

(10) Patent No.: US 9,814,562 B2
(45) Date of Patent: Nov. 14, 2017

(54) INTERFERENCE-RELIEF TYPE DELIVERY DETACHMENT SYSTEMS

(71) Applicant: COVIDIEN LP, Mansfield, MA (US)

(72) Inventors: Karl S. Halden, San Carlos, CA (US); Nicholas C. deBeer, Montara, CA (US); Frank P. Becking, Palo Alto, CA (US)

(73) Assignee: COVIDIEN LP, Mansfield, MA (US)

( * ) Notice: Subject to any disclaimer, the term of this patent is extended or adjusted under 35 U.S.C. 154(b) by 459 days.

(21) Appl. No.: 13/842,536

(22) Filed: Mar. 15, 2013

(65) Prior Publication Data

US 2013/0211495 A1 Aug. 15, 2013

Related U.S. Application Data

(63) Continuation-in-part of application No. 12/942,209, filed on Nov. 9, 2010, now Pat. No. 9,095,342.
(Continued)

(51) Int. Cl.
*A61M 29/00* (2006.01)
*A61F 2/06* (2013.01)
(Continued)

(52) U.S. Cl.
CPC .......... *A61F 2/06* (2013.01); *A61B 17/12022* (2013.01); *A61B 17/12109* (2013.01);
(Continued)

(58) Field of Classification Search
CPC .... A61F 2/0004; A61F 2/0022; A61F 2/0027; A61F 2/02; A61F 2/04; A61F 2/06;
(Continued)

(56) References Cited

U.S. PATENT DOCUMENTS

| | | |
|---|---|---|
| 4,655,771 A | 4/1987 | Wallsten |
| 5,109,867 A | 5/1992 | Twyford, Jr. |

(Continued)

FOREIGN PATENT DOCUMENTS

| | | |
|---|---|---|
| CN | 2456640 Y | 10/2001 |
| CN | 1652726 A | 8/2005 |

(Continued)

*Primary Examiner* — Jonathan Miles
*Assistant Examiner* — Kendra Obu
(74) *Attorney, Agent, or Firm* — Beth McMahon

(57) ABSTRACT

Various features are described that are adapted to improve performance of interference-relief type delivery systems. A delivery system provided herein comprises an implant comprising a socket at a proximal end of the implant; an elongate sleeve having (i) a proximal section, (ii) a distal section slidably disposed within the socket, and (iii) a window between the proximal section and the distal section, the window extending through a wall of the sleeve; and a core member having a proximal portion slidably received within the proximal section of the sleeve and a distal portion extending through the window to a space outside the sleeve and within the socket. The distal portion of the core member provides an interference fit with the distal section of the sleeve within the socket until the core member is withdrawn.

13 Claims, 11 Drawing Sheets

Related U.S. Application Data

(60) Provisional application No. 61/259,585, filed on Nov. 9, 2009.

(51) Int. Cl.

| | | |
|---|---|---|
| A61F 6/18 | (2006.01) | |
| A61F 6/14 | (2006.01) | |
| A61B 17/12 | (2006.01) | |
| A61F 6/20 | (2006.01) | |
| A61B 17/00 | (2006.01) | |
| A61B 90/00 | (2016.01) | |

(52) U.S. Cl.
CPC .. *A61B 17/12113* (2013.01); *A61B 17/12172* (2013.01); *A61B 17/0057* (2013.01); *A61B 17/12122* (2013.01); *A61B 17/12136* (2013.01); *A61B 17/12168* (2013.01); *A61B 17/12181* (2013.01); *A61B 90/39* (2016.02); *A61B 2017/12054* (2013.01); *A61F 6/146* (2013.01); *A61F 6/148* (2013.01); *A61F 6/18* (2013.01); *A61F 6/20* (2013.01)

(58) Field of Classification Search
CPC ...... A61F 2/01; A61F 2/013; A61F 2002/011; A61F 2002/015; A61F 2002/016; A61F 2002/061; A61F 2002/065; A61F 2002/068; A61F 2210/0076; A61F 2220/0008; A61F 2230/0063; A61F 2230/0065; A61F 2230/0071; A61F 2250/0009; A61F 2250/0023; A61F 2250/0024; A61F 2250/0028; A61F 2250/0051; A61F 5/0003; A61F 5/0013; A61F 5/003; A61F 5/0033; A61F 5/0036; A61F 5/004; A61F 5/0043; A61F 5/0046; A61F 6/146; A61F 6/148; A61F 6/16; A61F 6/18; A61F 6/20; A61F 6/202; A61B 17/12131; A61B 17/12145; A61B 17/12168; A61B 17/12172; A61B 17/0057; A61B 17/12022; A61B 17/12027; A61B 17/12036; A61B 17/1204; A61B 17/12099; A61B 17/12109; A61B 17/12113; A61B 17/12118; A61B 17/1214; A61B 17/12177; A61B 2017/00592; A61B 2017/00597; A61B 2017/00615; A61B 2017/00619; A61B 2017/00623; A61B 2017/00632; A61B 2017/00646; A61B 2017/00659; A61B 2017/1205; A61B 2017/12054; A61B 2017/12059; A61B 2017/12063; A61B 2017/12068; A61B 2017/12072; A61B 2017/12077; A61B 2017/12081; A61B 2017/12086; A61B 2017/1209; A61B 2017/12095; A61B 17/12122; A61B 17/12136; A61B 17/12181; A61B 2017/00575; A61B 2017/00601; A61B 2017/00637; A61B 2017/00641; A61B 2017/0065; A61B 2017/00654; A61B 2017/12127

See application file for complete search history.

(56) References Cited

U.S. PATENT DOCUMENTS

| | | |
|---|---|---|
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,282,806 A | 2/1994 | Haber et al. |
| 5,304,195 A | 4/1994 | Twyford, Jr. et al. |
| 5,312,415 A | 5/1994 | Palermo |
| 5,350,397 A | 9/1994 | Palermo et al. |
| 5,368,592 A | 11/1994 | Stern et al. |
| 5,417,708 A | 5/1995 | Hall |
| 5,480,382 A | 1/1996 | Hammerslag et al. |
| 5,490,859 A | 2/1996 | Mische et al. |
| 5,499,985 A | 3/1996 | Hein et al. |
| 5,562,698 A | 10/1996 | Parker |
| 5,669,905 A | 9/1997 | Scheldrup et al. |
| 5,728,129 A | 3/1998 | Summers |
| 5,800,455 A | 9/1998 | Palermo et al. |
| 5,814,062 A | 9/1998 | Sepetka et al. |
| 5,895,391 A | 4/1999 | Farnholtz |
| 5,989,242 A | 11/1999 | Saadat et al. |
| 6,004,338 A | 12/1999 | Ken et al. |
| 6,022,369 A | 2/2000 | Jacobsen et al. |
| 6,039,744 A | 3/2000 | Forber |
| 6,063,070 A | 5/2000 | Eder |
| 6,136,015 A | 10/2000 | Kurz et al. |
| 6,152,947 A | 11/2000 | Ambrisco et al. |
| 6,190,373 B1 | 2/2001 | Palermo et al. |
| RE37,117 E | 3/2001 | Palermo |
| 6,203,547 B1 | 3/2001 | Nguyen et al. |
| 6,270,508 B1 | 8/2001 | Klieman et al. |
| 6,375,668 B1 | 4/2002 | Gifford et al. |
| 6,397,850 B1 | 6/2002 | Scheldrup et al. |
| 6,464,699 B1 | 10/2002 | Swanson |
| 6,585,767 B1 * | 7/2003 | Holley ............... A61F 2/2409 623/2.41 |
| 6,589,236 B2 | 7/2003 | Wheelock et al. |
| 6,589,251 B2 | 7/2003 | Yee et al. |
| 6,656,351 B2 | 12/2003 | Boyle |
| 6,994,689 B1 | 2/2006 | Zadno-Azizi et al. |
| 7,018,394 B2 | 3/2006 | Diaz et al. |
| 7,022,133 B2 | 4/2006 | Yee et al. |
| 7,294,146 B2 | 11/2007 | Chew et al. |
| 7,331,973 B2 | 2/2008 | Gesswein et al. |
| 7,344,558 B2 | 3/2008 | Lorenzo et al. |
| 7,367,987 B2 | 5/2008 | Balgobin et al. |
| 7,371,252 B2 | 5/2008 | Balgobin et al. |
| 7,377,932 B2 | 5/2008 | Mitelberg et al. |
| 7,419,501 B2 | 9/2008 | Chiu et al. |
| 7,591,829 B2 | 9/2009 | Gibson et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,811,305 B2 | 10/2010 | Balgobin et al. |
| 7,901,444 B2 | 3/2011 | Slazas |
| 7,918,872 B2 | 4/2011 | Mitelberg et al. |
| 8,007,509 B2 | 8/2011 | Buiser et al. |
| RE42,758 E | 9/2011 | Ken et al. |
| 8,016,852 B2 | 9/2011 | Ho et al. |
| 8,029,466 B2 | 10/2011 | Wilson et al. |
| 8,034,073 B2 | 10/2011 | Davis, III et al. |
| 8,062,325 B2 | 11/2011 | Mitelberg et al. |
| 8,100,918 B2 | 1/2012 | Gandhi et al. |
| 8,142,456 B2 | 3/2012 | Rosqueta et al. |
| 8,333,796 B2 | 12/2012 | Tompkins et al. |
| 2001/0002438 A1 | 5/2001 | Sepetka et al. |
| 2001/0037141 A1 | 11/2001 | Yee et al. |
| 2002/0010481 A1 | 1/2002 | Jayaraman |
| 2002/0072712 A1 | 6/2002 | Nool et al. |
| 2002/0116024 A1 | 8/2002 | Goldberg et al. |
| 2002/0143348 A1 | 10/2002 | Wallace et al. |
| 2002/0165572 A1 | 11/2002 | Saadat et al. |
| 2003/0014073 A1 | 1/2003 | Bashiri et al. |
| 2003/0045901 A1 | 3/2003 | Opolski |
| 2003/0171770 A1 | 9/2003 | Kusleika et al. |
| 2003/0199966 A1 | 10/2003 | Shiu et al. |
| 2004/0002731 A1 | 1/2004 | Aganon et al. |
| 2004/0002733 A1 | 1/2004 | Teoh |
| 2004/0034363 A1 | 2/2004 | Wilson et al. |
| 2004/0087964 A1 | 5/2004 | Diaz et al. |
| 2004/0106946 A1 | 6/2004 | Ferrera et al. |

(56) References Cited

U.S. PATENT DOCUMENTS

| | | |
|---|---|---|
| 2004/0181256 A1 | 9/2004 | Glaser |
| 2004/0243228 A1 | 12/2004 | Kowalsky et al. |
| 2005/0021023 A1 | 1/2005 | Guglielmi et al. |
| 2006/0025792 A1 | 2/2006 | Gibson et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0106417 A1 | 5/2006 | Tessmer et al. |
| 2006/0116714 A1 | 6/2006 | Sepetka et al. |
| 2006/0155323 A1* | 7/2006 | Porter ............. A61B 17/12022 606/200 |
| 2006/0271097 A1 | 11/2006 | Ramzipoor et al. |
| 2006/0271099 A1 | 11/2006 | Marks et al. |
| 2006/0276823 A1 | 12/2006 | Mitelberg et al. |
| 2006/0276824 A1 | 12/2006 | Mitelberg et al. |
| 2006/0278680 A1 | 12/2006 | Viola et al. |
| 2007/0173757 A1 | 7/2007 | Levine et al. |
| 2007/0179520 A1 | 8/2007 | West |
| 2007/0185524 A1 | 8/2007 | Diaz et al. |
| 2007/0221230 A1 | 9/2007 | Thompson et al. |
| 2007/0239193 A1 | 10/2007 | Simon et al. |
| 2007/0265656 A1* | 11/2007 | Amplatz ............ A61B 17/0057 606/200 |
| 2007/0267281 A1 | 11/2007 | Smith |
| 2007/0270936 A1 | 11/2007 | Andreas et al. |
| 2007/0282373 A1 | 12/2007 | Ashby et al. |
| 2008/0033478 A1* | 2/2008 | Meng ................ A61B 17/0057 606/194 |
| 2008/0045997 A1 | 2/2008 | Balgobin et al. |
| 2008/0097462 A1 | 4/2008 | Mitelberg et al. |
| 2008/0119886 A1* | 5/2008 | Greenhalgh ....... A61B 17/0057 606/200 |
| 2008/0119887 A1 | 5/2008 | Que et al. |
| 2008/0228215 A1 | 9/2008 | Strauss et al. |
| 2008/0243106 A1 | 10/2008 | Coe et al. |
| 2008/0255542 A1 | 10/2008 | Nimgaard et al. |
| 2008/0281350 A1 | 11/2008 | Sepetka et al. |
| 2008/0300616 A1 | 12/2008 | Que et al. |
| 2008/0306504 A1 | 12/2008 | Win et al. |
| 2009/0012554 A1 | 1/2009 | Makower et al. |
| 2009/0018653 A1 | 1/2009 | Bashiri et al. |
| 2009/0024154 A1 | 1/2009 | Williams et al. |
| 2009/0062812 A1 | 3/2009 | Fitz et al. |
| 2009/0076623 A1 | 3/2009 | Mathis et al. |
| 2009/0088832 A1 | 4/2009 | Chew et al. |
| 2009/0112239 A1 | 4/2009 | To et al. |
| 2009/0138036 A1 | 5/2009 | Nardone et al. |
| 2009/0163780 A1 | 6/2009 | Tieu |
| 2009/0163986 A1 | 6/2009 | Tieu et al. |
| 2009/0177261 A1 | 7/2009 | Teoh et al. |
| 2009/0182268 A1 | 7/2009 | Thielen et al. |
| 2009/0254169 A1 | 10/2009 | Spenser et al. |
| 2009/0270877 A1 | 10/2009 | Johnson et al. |
| 2009/0275974 A1* | 11/2009 | Marchand ........ A61B 17/12022 606/194 |
| 2009/0287291 A1 | 11/2009 | Becking et al. |
| 2009/0306706 A1* | 12/2009 | Osypka .............. A61B 17/0057 606/213 |
| 2009/0312748 A1 | 12/2009 | Johnson et al. |
| 2010/0004673 A1 | 1/2010 | Denison et al. |
| 2010/0030200 A1 | 2/2010 | Strauss et al. |
| 2010/0094395 A1 | 4/2010 | Kellett |
| 2010/0174269 A1 | 7/2010 | Tompkins et al. |
| 2010/0234872 A1 | 9/2010 | Guo et al. |
| 2010/0256666 A1 | 10/2010 | Chen et al. |
| 2010/0268204 A1 | 10/2010 | Tieu et al. |
| 2010/0268251 A1 | 10/2010 | Chen et al. |
| 2010/0268252 A1 | 10/2010 | Chen et al. |
| 2011/0022003 A1 | 1/2011 | Tekulve |
| 2011/0106098 A1 | 5/2011 | Williams |
| 2011/0106128 A1 | 5/2011 | Chen |
| 2011/0118772 A1 | 5/2011 | Chen et al. |
| 2011/0118776 A1 | 5/2011 | Chen et al. |
| 2011/0172700 A1 | 7/2011 | Bose et al. |
| 2011/0202085 A1 | 8/2011 | Loganathan |
| 2011/0208227 A1 | 8/2011 | Becking |
| 2011/0265943 A1 | 11/2011 | Rosqueta et al. |
| 2011/0282380 A1 | 11/2011 | Davis et al. |
| 2011/0301686 A1 | 12/2011 | Bowman et al. |
| 2011/0313447 A1 | 12/2011 | Strauss |
| 2011/0319926 A1 | 12/2011 | Becking et al. |
| 2012/0041470 A1 | 2/2012 | Shrivastava et al. |
| 2012/0041472 A1 | 2/2012 | Tan et al. |
| 2012/0046687 A1 | 2/2012 | Trommeter et al. |
| 2012/0065720 A1 | 3/2012 | Strauss |
| 2012/0101510 A1 | 4/2012 | Lenker et al. |
| 2012/0226305 A1 | 9/2012 | Strauss |
| 2012/0316598 A1 | 12/2012 | Becking et al. |
| 2012/0330347 A1 | 12/2012 | Becking et al. |
| 2013/0066360 A1 | 3/2013 | Becking et al. |
| 2013/0085520 A1 | 4/2013 | Liang |
| 2013/0085521 A1 | 4/2013 | Lim |
| 2013/0085522 A1 | 4/2013 | Becking et al. |
| 2013/0123830 A1 | 5/2013 | Becking et al. |
| 2013/0138136 A1 | 5/2013 | Beckham |
| 2013/0211495 A1 | 8/2013 | Halden |

FOREIGN PATENT DOCUMENTS

| | | |
|---|---|---|
| CN | 1668250 A | 9/2005 |
| CN | 101234034 A | 8/2008 |
| CN | 101835430 A | 9/2010 |
| CN | 102119004 A | 7/2011 |
| CN | 102791205 A | 11/2012 |
| DE | 19547617 | 9/1997 |
| EP | 7179690 A2 | 6/1996 |
| EP | 829236 | 3/1998 |
| EP | 853 955 | 7/1998 |
| EP | 996372 | 5/2000 |
| EP | 1400208 | 3/2004 |
| EP | 1487526 | 12/2004 |
| EP | 1621150 A2 | 2/2006 |
| EP | 1738698 A2 | 1/2007 |
| EP | 832 607 | 4/2008 |
| JP | 09-149904 | 6/1997 |
| JP | 10-201766 | 8/1998 |
| JP | 2004/073874 A | 3/2004 |
| JP | 2004-267749 A | 9/2004 |
| JP | 2006-051349 A | 2/2006 |
| JP | 2009-533202 A | 9/2009 |
| WO | WO-92/21400 | 12/1992 |
| WO | WO-93/11719 | 6/1993 |
| WO | WO-94/06502 A2 | 3/1994 |
| WO | WO-98/34546 | 8/1998 |
| WO | WO-98/58590 | 12/1998 |
| WO | WO-01/58382 | 8/2001 |
| WO | WO-02/054943 A2 | 7/2002 |
| WO | WO-2004/087006 A3 | 11/2004 |
| WO | WO-2007/070797 A2 | 6/2007 |
| WO | WO-2007/121405 | 10/2007 |
| WO | WO-2008/112435 | 9/2008 |
| WO | WO-2008/127525 A1 | 10/2008 |
| WO | WO-2010/009019 | 1/2010 |
| WO | WO-2010/117883 | 10/2010 |
| WO | WO-2010/123821 | 10/2010 |

* cited by examiner

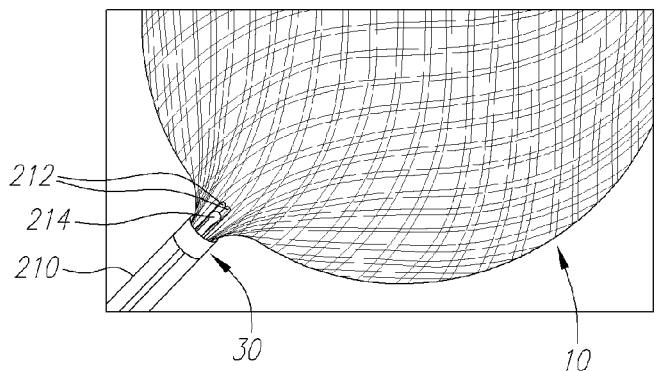
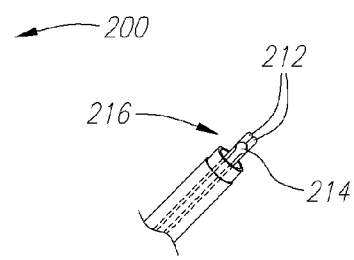
FIG. 20A
FIG. 18
FIG. 19A
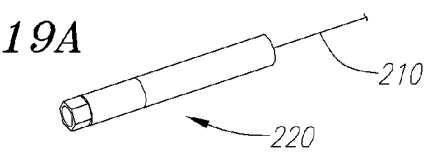
FIG. 20B
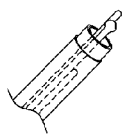
FIG. 19B
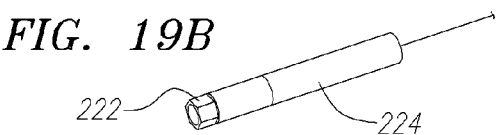
FIG. 20C
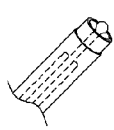
FIG. 19C
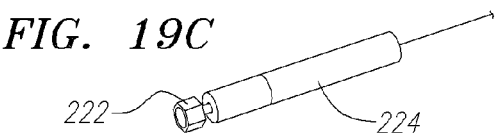
FIG. 20D
FIG. 19D
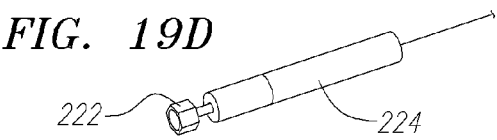
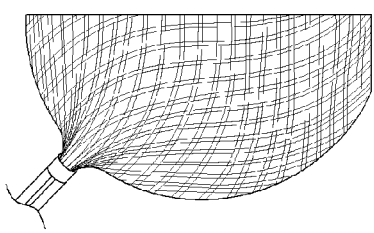
FIG. 19E
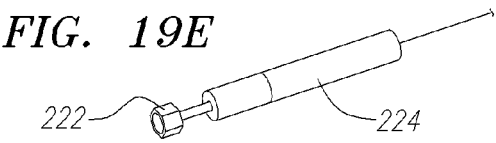
FIG. 20E

INTERFERENCE-RELIEF TYPE DELIVERY DETACHMENT SYSTEMS

RELATED APPLICATIONS

This application is a continuation-in-part of U.S. application Ser. No. 12/942,209, filed Nov. 9, 2010, which claims priority to U.S. Provisional Application Ser. No. 61/259,585, filed Nov. 9, 2009, each of which is incorporated herein by reference in its entirety.

FIELD

The present application relates to delivery systems, methods, and configurations for implanting a device within a body of a patient.

BACKGROUND

Braid-based embolization devices and delivery system interfaces may be used for occluding blood flow at endovascular sites. One use is in intracranial aneurysm embolization or occlusion and another in parent vessel occlusion (PVO) or sacrifice.

SUMMARY

Braid-ball devices formed with folded-over and folded-flat distal ends are among the architectures described in Becking, et al. These architectures are some of the ones best suited for treating brain aneurysms. Distal marker approaches are described that are especially suited for such devices. In addition, proximal end finishing approaches are described that are suitable for these and the rest of the devices described in Becking et al. Likewise, all of the features and technologies presented in Becking, et al. (PCT/US2009/041313) are incorporated herein by reference.

Regarding the distal marker approaches, one improvement comprises a tether to/for the distal marker included in the implant. Specifically, with the marker affixed adjacent to the distal end of the implant (as in the folded-flat embodiments in the incorporated application), the length of the tether/tie extends to the proximal hub of the implant. It has a length set so that when the implant is compressed, the marker is pulled into alignment with the implant and/or catheter.

When a suture is employed for the tether, it can tie around the interior of the distal fold with minimal interference. However, it may be advantageous to use a wire ribbon (e.g., Pt or Nitinol) for other reasons.

Namely, a tether ribbon (especially when pre-formed into a "V" shape) can be threaded through the gap/hole and around as few as one wire from the braid. So-disposed, there is no interference with the compression of the distal end of the implant. What is more, spring action in the ribbon tether (whether comprising two filaments or trimmed to one after crimping, gluing, welding or otherwise affixing at least one marker) can help position the marker against/across the top of the implant when deployed. Such a ribbon can also contribute to marker radiopacity, thereby allowing a smaller marker size.

Another option is to include fibers and/or other thrombus promoting material in connection with the tether. Whatever material option is selected and/or additional features are provided, the proximal end of the tether is advantageously captured between the layers of braid or between the braid and either one of optional inner or outer bands. It may be glued-in, affixed by welding or otherwise.

Yet another set of improvements concerns the manner in which the implant is finished. By "finished", what is meant is the manner in which the proximal side of the implant is managed to define a hub and/or delivery system detachment interface.

In one advantageous approach, in which use of an inner band is desired for interface with detachment system components (such as those described in the referenced application), processing is done with an elongate hypotube set within the braid. The hypotube (e.g., about 2-5 cm long) serves as a means to hold and manipulate an implant preform construct. In addition, when the tube is trimmed off (or when the final or near-final implant is trimmed off relative to the tube being held) the remaining portion of the hypotube within the implant (now the "inner band") defines the detachment interface lumen. Likewise—especially when a more radiopaque material such as Pt/Ir or CoCr is used for the tube, the same structure will improve and/or offer the requisite radiopacity at the proximal end of the implant.

In all, the approach (optionally characterized as a "sacrificial hypotube length" approach) is useful for gluing but may also be applied in a welding technique. In fact, it may be especially useful in the latter context by providing shielding from weld slag and deformation for the proximal aperture/port to be exposed by trimming the tube to define the inner band in the implant. Namely, after welding, a clean cut can be made (e.g., with a diamond saw, laser cutting, EDM, etc.—as above) and then any deburring (by mechanical action, etching, EP or otherwise) can be performed on the newly-exposed face as desired.

In conjunction with a sacrificial hypotube length approach for gluing, or the original gluing approach described in the referenced application, another advantageous option is offered by a different post-processing step. Namely, after an outer band is used at the proximal end of the implant to define an outer casting boundary for adhesive/glue (e.g., Loctite 4014), it then may be removed leaving the underlying glue casting in place. Outer band removal offers potential to reduce all of the height, diameter and appearance of the size of the proximal feature of the implant. Accordingly, it may assist in developing a system with 0.021" catheter crossing profile.

To facilitate removal, the band may advantageously comprise NiTi alloy (that naturally forms a passivation layer) or it may be coated or otherwise plated. A Titanium Nitride coating may be desirable. Spray mold release (e.g., 3M) or dip-coating in mold release may alternatively be employed to assist in slipping-off the band after adhesive application and curing. Otherwise, the band can be cut off the glue casting.

Another approach for achieving minimal implant hub diameter—while maintaining necessary radiopacity—involves affixing a platinum band on top of an inner NiTi band (i.e., in a linear arrangement). The proximal/lower NiTi section can be easily welded to the NiTi braid in the ball (when so-constructed) and the Pt (including Pt/Ir and other alloys) provides an in-line radiopaque marker. The detachment system control and anchor wires are received through both bands. The bands may be attached (e.g., by welding, gluing or soldering) or merely associated with each other until detachment system wire removal. In either case, they may include interference fit, puzzle-piece or other groove or tongue-and-groove features to make or assist in making a connection between the bodies.

Another set of improvements concerns shaping the distal end of a "folded-flat" type implant. It may be provided with a flattened top. The flattened top derives from a flat formed in the round tooling over which the braid is shaped. The flat can be produced by milling about 0.010" off the form. This depth cut allows sufficient "table" for desired shaping and can be consistently applied across a range of implants sized from about 5 mm to 12 mm in diameter with little effect on the perceived shape. The resulting crease in the implant wire shaped by such a form offers an immediate advantage to implant deployment. With the flat placed so close to the distal end of the device, shape recovery of the bend/crease around the flattened top drives early opening of the implant when unsheathed (as compared to a situation where a crease formed around the flat is set further away—or none is provided).

Yet another set of implant improvements described herein augments the density of the ball. Stated otherwise, provision is made for an additional layer of braid material to further decrease the braid matrix porosity, and possibly do so without any increase in device crossing profile/delivery (micro)catheter compatibility.

These improvements involve a third layer of braid that is added to the two layers preferably already present in the folded-flat base implant architecture. In one variation, a third layer of braid is captured between the two layers and captured within the hub region, but trimmed proximal to the distal folded-over/flat section. In another variation, an inner layer is set within the envelope of the aforementioned two layers. It is advantageously attached to a distal end of the inner marker band (above/distal) to any outer marker band provided. As such, the braid's attachment will not increase the hub profile. To avoid any profile increase at the distal end of the implant, the inner layer will typically be trimmed so its compressed length is located proximal to the folded-over braid at the distal end of the implant when compressed. In its unconstrained form, the inner layer may simply define a cup. Alternatively, it may define a secondary ball shape. Such a ball shape may be substantially spherical or ovoid. One advantageous configuration further includes unterminated distal ends to the braid. The ends of the braid defining the inner ball may be secured in a band or welded together. So-configured they can offer another radiopaque marker feature within the ball. However, it may be preferred that the braid ends of the inner layer (in cup, ball form, or otherwise) are unterminated. As such, they may improve thrombus formation within the body of the implant.

Finally, delivery system improvements are described. The features described are "improvements"—as are the features noted above—in a contextual sense. For example, certain of the delivery system architectures may not be as space-efficient as others. Yet, such larger system(s) may be desirable for reason of reduced manufacturing complexity and/or cost.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

1. A delivery system, comprising:
an implant comprising a socket at a proximal end of the implant;
an elongate sleeve having (i) a proximal section, (ii) a distal section slidably disposed within the socket, and (iii) a window between the proximal section and the distal section, the window extending through a wall of the sleeve; and
a core member having a proximal portion slidably received within the proximal section of the sleeve and a distal portion extending through the window to a space outside the sleeve and within the socket;
wherein the distal portion of the core member provides an interference fit with the distal section of the sleeve within the socket until the core member is withdrawn.
2. The delivery system of clause 1, wherein the core member is a round wire and each of the socket, the proximal section of the sleeve, and the proximal portion of the core wire are coaxially aligned.
3. The delivery system of clause 1, wherein at least a portion of the distal section of the sleeve and at least a portion of the distal portion of the core member are axially aligned and radially adjacent.
4. The delivery system of clause 1, wherein the core wire includes a distal ball.
5. The delivery system of clause 1, wherein the sleeve includes a distal ball.
6. The delivery system of clause 1, wherein the sleeve comprises a plurality of cutouts along a length of the sleeve.
7. The delivery system of clause 5, wherein the plurality of cutouts are positioned on alternating sides of the sleeve.
8. The delivery system of clause 1, further comprising an insert in the distal section of the sleeve.
9. The delivery system of clause 1, wherein the insert defines a surface oriented obliquely with respect to a central axis of the sleeve
10. The delivery system of clause 9, wherein a side of the surface connects to the window.
11. The delivery system of clause 9, wherein distally directed forces of the core member against the surface deflect core member through the window.
12. The delivery system of clause 1, wherein the distal section of the sleeve defines a surface oriented obliquely with respect to a central axis of the sleeve.
13. The delivery system of clause 12, wherein distally directed forces of the core member against the surface deflect core member through the window.
14. The delivery system of clause 12, wherein a side of the surface connects to the window.
15. The delivery system of clause 1, wherein the core member comprises a ribbon, a portion of the ribbon lying flat against insert.
16. A method, comprising:
guiding a delivery system to an implant site;
withdrawing a distal portion of a core member from an interference fit with a distal section of a sleeve within a socket of an implant, such that the distal portion is retracted through a window to be within a proximal section of the sleeve;
withdrawing the sleeve from the socket, such that the implant is disengaged from the core member and the sleeve.
17. The method of clause 16, wherein, while guiding the delivery system to the implant site, the distal portion of the core member is maintained in an interference fit with the distal section of the sleeve within the socket of the implant.

18. A method of assembling a delivery system, comprising:
    inserting a distal section of an elongate sleeve into a socket of an implant;
    inserting a distal portion of a core member through the sleeve;
    passing the distal portion of the core member through a window of the sleeve;
    engaging the distal portion of the core member into an interference fit with the distal section of the sleeve within the socket of the implant.
19. The method of clause 18, wherein passing the distal portion of the core member through the window comprises providing a distally directed force to the core member, such that the core member is deflected by a surface of the distal section of the sleeve oriented obliquely with respect to a central axis of the sleeve.

The subject implant and delivery devices, kits in which they are included, methods of use and manufacture are all included within the scope of the present description. A number of aspects of such manufacture are discussed above. More detailed discussion is presented in connection with the figures below.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 18 shows an overview of an implant/detachment system interface as may be employed in connection with the present invention.

FIGS. 19A, 19B, 19C, 19D, 19E, 20A, 20B, 20C, 20D, and 20E illustrate the stages of operation (handle-side and implant-side, respectively) of the system shown in FIG. 18.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1A:
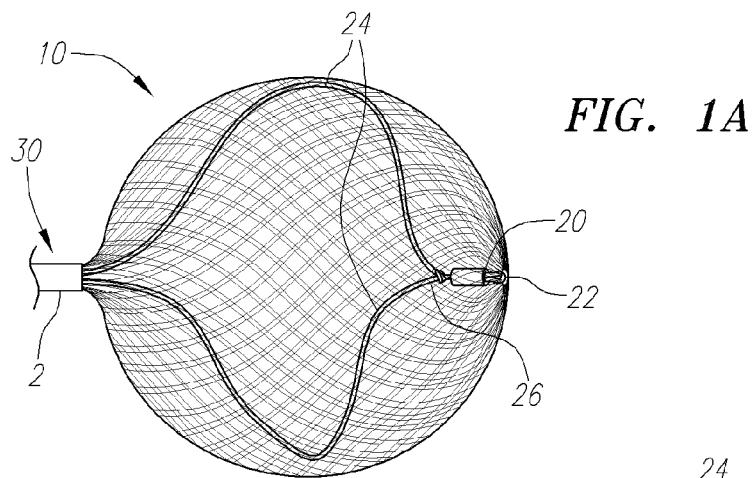
FIGS. 1A and 1B show an implant with a marker tether as expanded and being compressed, respectively.
Figure 1B:
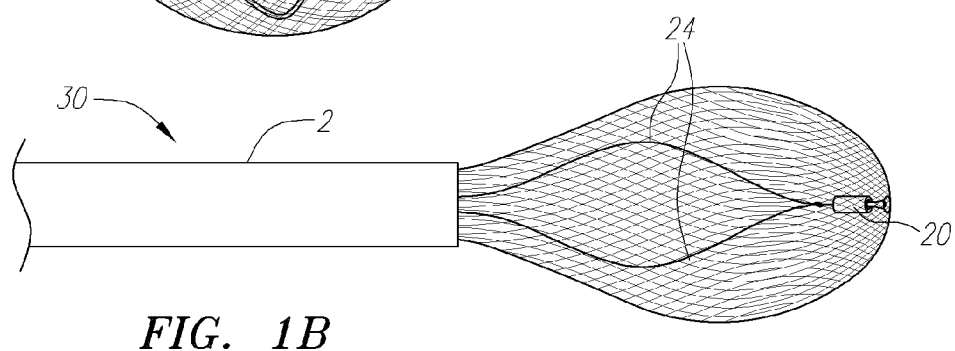

Turning to the figures, FIGS. 1A and 1B show an implant 10. In FIG. 1A, only the hub (not visible) of implant 10 is received within a sheath or catheter 2. Roughly 40% of implant 10 is received within sheath 2 in FIG. 1B. A radiopaque marker 20 (e.g., a Pt band) is visible in both views. As in Becking, et al., and with further reference to FIG. 4, implant 10 includes a tie 22 positioned between braid layers 12 and 14 adjacent a distal fold 16 in the braid, which defines aperture 18 (also referred to herein as the hole or gap in the braid). Marker 20 is held by tie 22. Tie 22 may also assist in closing or limiting the size to which aperture 18 may open.

While tie 22 terminates adjacent marker 20 in Becking et al., it extends to proximal hub 30 of implant 10 in the present description. The extension "tether" portions, or members, 24 so-provided operate to ensure axial alignment of marker 20 when implant 10 is captured (especially when re-capturing) in a catheter/sheath.

The length of tether member(s) 24 is therefore set such that slack is present when the implant is expanded (as shown in FIG. 1A) and the slack is removed when the implant is fully compressed or tending thereto (as shown in FIG. 1B).

Whereas the tie and/or tether member shown in FIGS. 1A and 1B is typically made of suture material, it may be made of any other biocompatible material including stainless steel, titanium, Nitinol (possibly wire that is martensitic at body temperature—commonly referred to as "muscle wire"), and the like. When suture material is employed it can tie around the interior of distal fold 16 with minimal interference and be knotted at point 26 (see FIG. 1A) to easily secure the position of marker 20. The same approach may be accomplished with fine wire (e.g., 0.001 inch round wire.)

It may instead be advantageous to use a wire ribbon (e.g., Pt or Nitinol) for other reasons. A construction as detailed in the next figures was made using a superelastic NiTi ribbon with dimensions set at about 0.001 inches by about 0.003 inches.

Figure 2A:
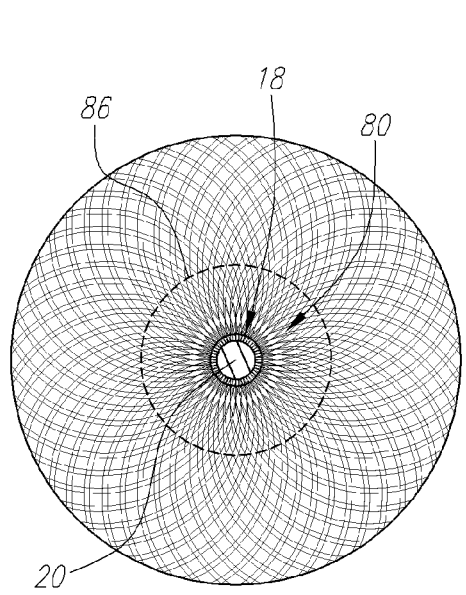
FIGS. 2A and 2B show the distal end and a side view of another tethered-marker embodiment, respectively.
Figure 2B:
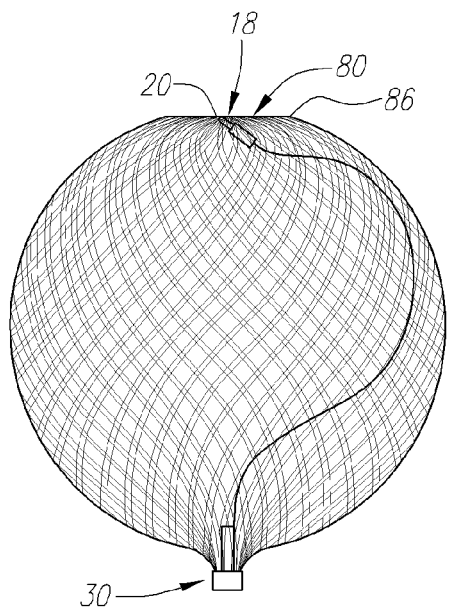
Figure 3:
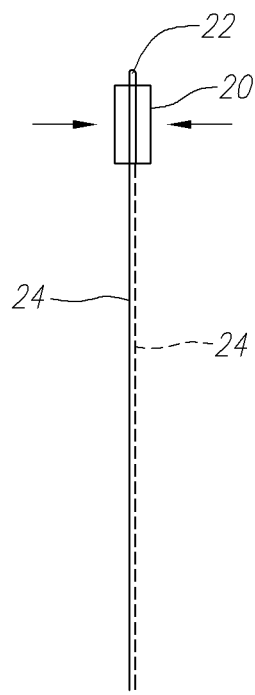
FIG. 3 shows a detail view of a marker/tether subassembly.
Figure 4:
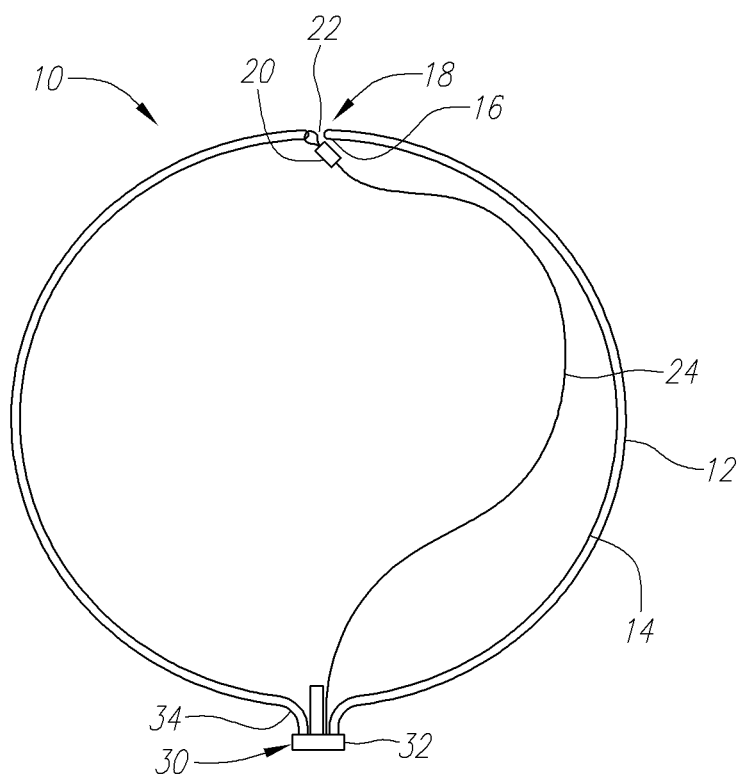
FIG. 4 diagrammatically illustrates the assembly in FIG. 3 set within an implant.

A tether ribbon 24 heatset into a tight loop or "V" shape was threaded through gap 18 and around as few as one wire from the braid at a distal end of implant 10 as shown in FIG. 4. So-disposed, tether ribbon 24 does not substantially interfere with compression of the distal end of the implant. What is more, spring action in the tether ribbon (whether comprising two filaments or trimmed to just one filament (as indicated by the broken line) after crimping, gluing, welding or otherwise affixing marker 20 as shown in FIG. 3) can help position marker 20 against (or across) the top of implant 10 when deployed, as shown in FIGS. 2A and 2B. As for affixing the marker, it is notable that the paired ribbon sections, stacked upon each other, provide a good interface upon which to crimp marker 20 without drastically altering the marker's shape.

Also, the length of the tether may optionally be set in a general "question-mark" shape to match (or more closely match) the curvature of the implant when unconstrained (e.g., as the tether appears in FIG. 4). Pre-shaping the tether to "match" (or approximately match) one or more implant sizes can help ensure predictable and similar performance of implants across a range of different implant sizes and compressions.

Figure 5:
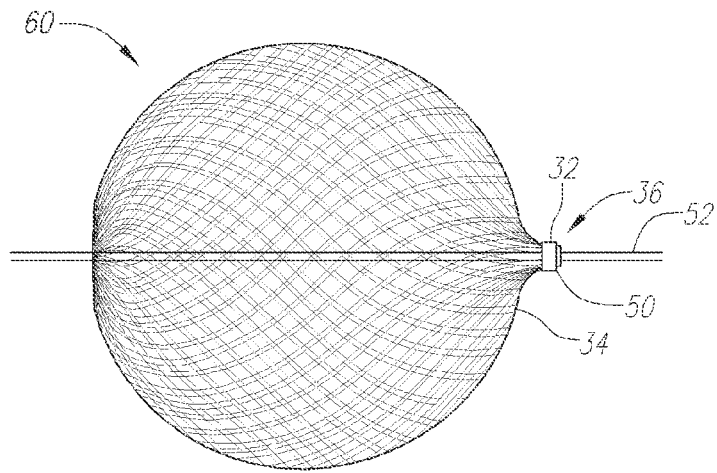
FIG. 5 shows an implant preform prepared for proximal end finishing.

As stated above, another improvement to the subject implants concerns the manner of proximal end finishing. FIG. 5 shows an implant preform 60 prepared for finishing of the proximal end 36. Here, implant preform 60 such as prepared in Becking, et al. is prepared, leaving an additional overhang section 50 extending past a proximal marker band 32. In many respects, the setup resembles that shown in FIG. 13A of Becking et al. with the implant preform 60 including an inner NiTi band 34 and the assembly set upon a mandrel 52. To maintain the position of the components as shown, glue (e.g., Loctite 4014) is applied. Even so, and referring also to FIG. 6, the hub region 30 can be welded effectively with a weld bead 53 incorporating the overhanging braid 50, inner band 34 and at least tack-welding an outer Pt band 32. It is noteworthy that achieving such a near-optimal welding result through (or into) the glue stabilized braid was a surprising result. In other words, it was neither predictable nor expected by those of skill in the art of welding (laser or otherwise). In any case, the length of the braid overhang incorporated into weld 53 may vary depending on a number of factors including implant diameter, wire diameter, braid density, etc. As shown, the overhang is about 0.005 to about 0.010 inches in length.

Figure 7:
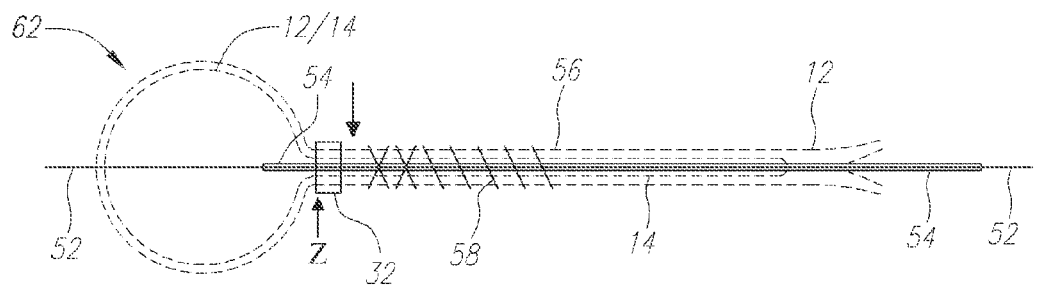
FIG. 7 shows an implant preform prepared for proximal end finishing according to another approach.

Another proximal end finishing approach is described in connection with FIG. 7. Specifically, preform 62 is not trimmed and stabilized for welding as shown in FIG. 5. Rather, preform 62 is prepared upon an elongate hypotube 54. The hypotube body provides a means to hold the construct and stabilize its elongate "tail" section 56 of braid layer 12 and/or layer 14 (e.g., by a wrap 58) thereon.

With a narrow window defined (e.g., with about 0.010 to about 0.025 inches of—preferably—exposed braid) laser energy is applied as indicated by the larger area. The energy is sufficient to weld the braid to the hypotube. The welding process does not, however, weld the hypotube to the optional underlying mandrel 52.

Figure 8:
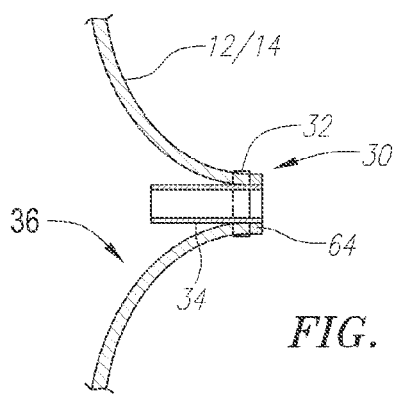
FIG. 8 shows the proximal end cut and welded.

After such welding, the majority of the length of hypotube 54 is "sacrificed". It is trimmed off of the proximal end 36 to define the inner band 34 of the implant as shown in FIG. 8. This inner band may provide some or all of the radiopacity required in the hub region 30 of the proximal end 36. However an outer band (especially if it comprises Pt) can be tack welded to the braid as indicated by the arrow Z in FIG. 7.

Figure 6:
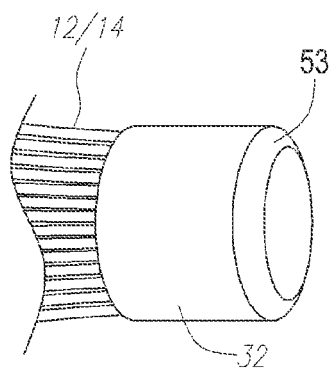
FIG. 6 shows the proximal end welded.

Irrespective of whether an outer marker band is included, FIG. 8 illustrates an advantage of the finishing approach, namely, the avoidance of weld bead flow artifacts associated with surface tension at the end of a body (as seen in FIG. 6). Rather, the weld 64 is neatly faced and the inner lumen of the remaining band 34 de-burred and/or reamed. Both actual and apparent hub size can be minimized accordingly.

Figure 9A:
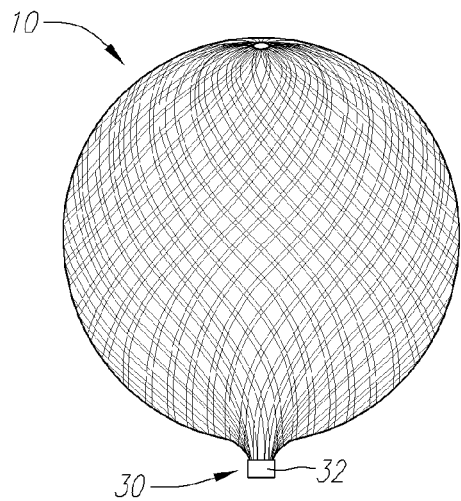
FIGS. 9A and 9B show implants employing alternative proximal end finishing approaches, with a detail view in FIG. 9B of a low-profile embodiment.
Figure 9B:
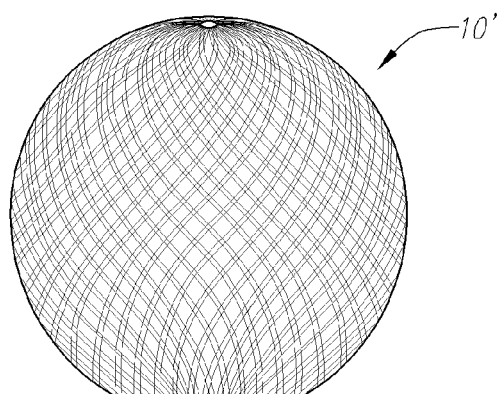

FIGS. 9A and 9B illustrate another advantageous proximal end finishing approach for minimizing proximal hub size. FIG. 9A shows an implant with an outer marker band 32 as it will generally appear as affixed by glue or welding. In instances where such a band is affixed by glue, once a glue cast is formed therein the band can be removed. An implant 10' will then include a proximal hub 30' that is reduced in diameter (by as much as about 0.004 inches depending on band thickness) and is also less noticeable by offering less contrast. Outside the body (e.g., in packaging) a physician will see a glaze or sheen of adhesive/glue 70 as a cast 72 in which the braid is embedded instead of a high contrast marker 32.

While seemingly unimportant to function, this visual aspect can indeed be relevant. The impression of physicians regarding the bulk of the proximal feature can affect whether the physician adopts the product. Conventional implants have been designed with the proximal hub completely inset within the inner volume of the implant. This is done to make the implant's appearance more attractive to physicians. However, the implant suffers in performance as a result (e.g., the implant is more difficult to recapture; the requirements on the implant's wire size and strength are heightened to force the implant to recover the inset shape, leading to an undesirable increase in implant dimension; and other performance deficiencies). In the present aspect of the invention, the perceived hub size is reduced, which increases the visual appeal without compromising performance.

Figure 10A:
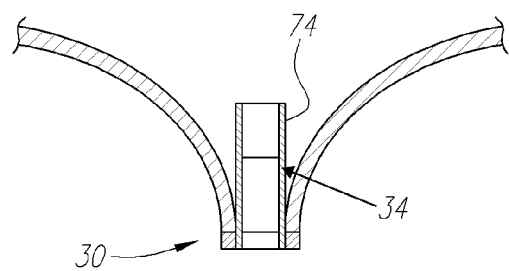
FIGS. 10A and 10B show additional proximal end radiopaque features as may be employed with various end-finishing approaches.
Figure 10B:
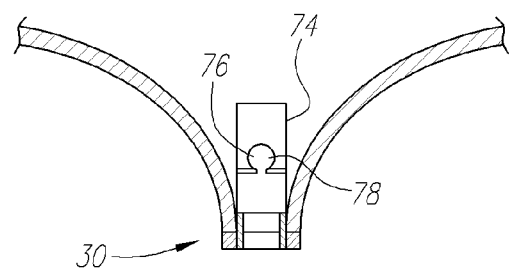

FIGS. 10A and 10B illustrate additional embodiments that eliminate the outer band while providing relatively increased radiopacity. Specifically, minimal implant hub size can be achieved by relocating a radiopaque band feature to an in-line arrangement with the inner band 34. A simple Pt band 74 can be set atop the inner band 34 as shown in FIG. 10A. These members may be joined using conventional techniques (i.e., gluing, soldering, welding, etc.) or be held in relation to one another on a temporary basis by utilizing delivery system interface members as shown in FIG. 18, etc. to the embodiment of FIG. 10B interlocks members 34 and 74 through the use of lock 76 and key 78 features.

Figure 11:
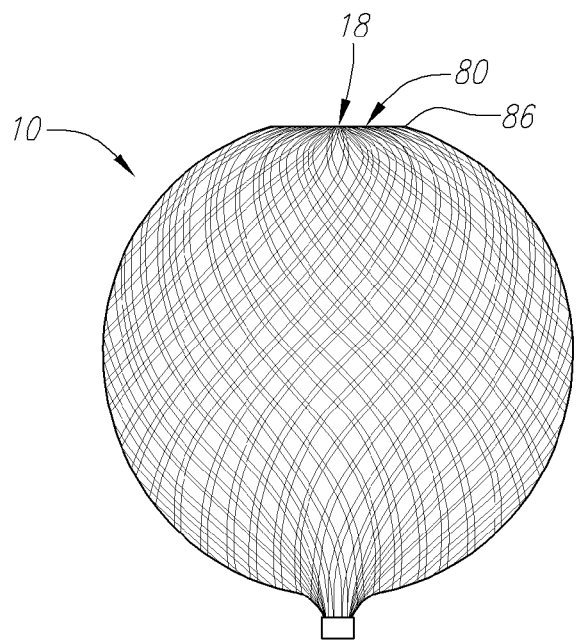
FIG. 11 shows in implant formed with a distal flattened top.
Figure 12:
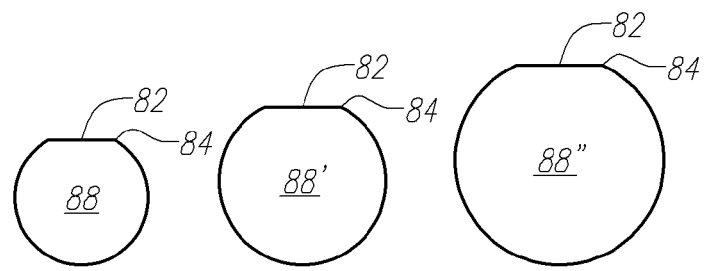
FIG. 12 shows implant forms for imparting an implant shape as shown in FIG. 11 across a number of different implants of a given size range.

Another implant feature is illustrated in connection with FIGS. 11 and 12. The implant optionally includes a flattened top 80 adjacent distal aperture 18. The flattened top is generated by providing a table surface 82 in the molding element 88 used to define the bulk shape of the implant. Molding elements, or "forms," in different sizes 88, 88' and 88" are shown in FIG. 12. They are milled down from a spherical form to define flat 82 surrounded by edge 84. The edge produces a crease 86 in the braid wire. Note that flat 80 and crease 86 are shown in alternate views in FIGS. 2A and 2B.

Figure 13A:
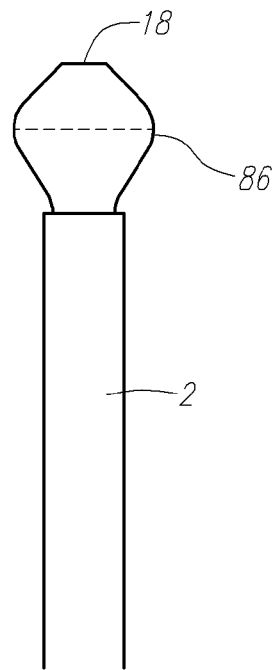
FIGS. 13A and 13B, respectively, illustrate the operation of an implant shaped according to FIG. 11/12 as compared to one that is not.
Figure 13B:
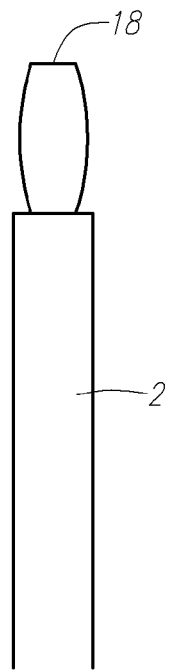

During implant preform heatsetting, it has been found that the flat section improves the quality of the distal fold 16 in the implant, helping to maximize uniformity and minimize the bend radius in the wires. As such, device trackability through tortuous anatomy within a catheter is also improved. The crease at the edge of the flattened area set in the implant also helps with delivery performance upon deployment. Specifically, as illustrated in FIG. 13A, the crease 86 represents multiple bends in the wires forming the implant braid matrix. Upon exit from the microcatheter, the bends recover and cause the implant distal end to open more than an implant without such a crease as shown in FIG. 13B (see also, the implant in FIG. 1B). As a more open body, the implant is softer, with more relaxed braid angle should it contact any fragile tissue—such as the dome of an aneurysm.

Other architectural changes or augmentations that may be applied to implants are shown in FIGS. 14-17. Each approach offers the potential for diagrammatically improved density relative to the parent architecture illustrated in FIG. 4.

Specifically, implant 90 includes an intermediate braid layer 92 set between outer layer 12 and inner layer 14. Layer 92 is captured in hub 30 as are the other layers at a proximal attachment 94. The distal extent 96 can be set at a number of positions. Advantageously, it extends to around the halfway point or equator of the device. This way, the layer will contribute to implant density (or—stated otherwise—reduce porosity) even for wide-neck aneurysms.

Figure 14:
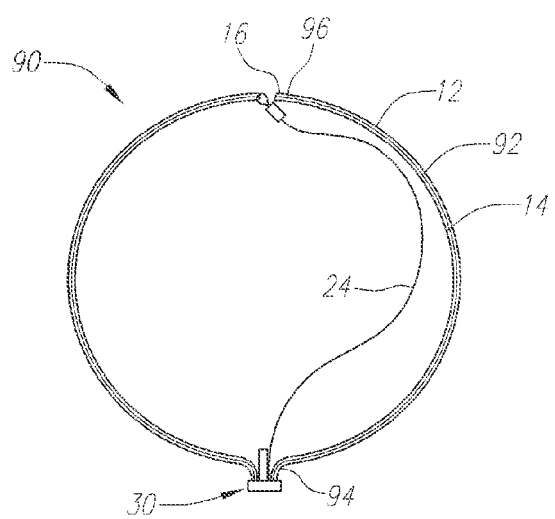
FIGS. 14, 15, 16, and 17 diagrammatically illustrate improved density implants as compared to the architecture presented in FIG. 4.

As shown in FIG. 14, the distal extent 96 of the braid is adjacent to the folded-over section 16 of the implant. Here, the density is highest so the inner layer wires will tend to stay best trapped between layers 12 and 14. Yet, since the distal extent 96 of the braid does not interfere with the fold 16 (which can be the highest profile aspect of the implant) little or no increase in crossing profile need result.

In production, the inner layer 12 of the implant can be produced simply by cutting a preform (like preform 62) in half at the distal fold. This produces a set of two inner layer sections that can be used in two different devices from a single formation procedure. However produced, because the inner layer may rely on the other layers for structural definition, it may be made of finer wire and/or with lower braid count than the other layers. For instance, the inner layer may comprise 72-end 0.0008 inch wire braid, whereas the outer layers comprise 96-end 0.0008 inch wire braid. However, the reverse may be true, in which the inner layer is more robust. In any case, it may be advantageous to mismatch the number of wire ends included in the braid (such as in the example directly above) to help avoid wire match-up, thereby minimizing porosity.

Figure 15:
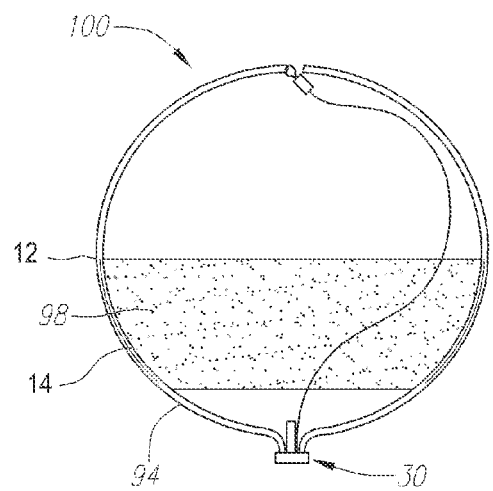

Implant 100 shown in FIG. 15 illustrates another advantageous approach to improving flow disruption effect, without increasing device crossing profile. As in device 90, an intermediate braid layer 98 is employed. However its proximal end is not secured within the hub, thereby easing space constraints in that region.

Instead, braid matrix integrity is maintained by coating the braid layer with a polymer (e.g., TICOPHILIC coating by Lubrizol, Inc.) or other coatings or processing. Hydrogel coating also offers an appealing option, such as a hydrogel-based polymer network capable of entrapping therapeutic agents as described in U.S. Pat. No. 6,905,700 to Won et al. Likewise, while the implant elements advantageously comprise Nitinol braid (typically superelastic NiTi), the braid used for any of the layers may instead comprise polymer—especially high strength biodegradable polymer such as MX-2 (MAX-Prene), synthetic absorbable monofilament (90/10 Glycolide/L-Lactide) and/or G-2 (Glycoprene), synthetic absorbable monofilament (Glycolide (PGA), ϵ-Caprolactone (PCL), Trimethylene Carbonate (TMC) Copolymer) that is heat set into shape (e.g., at 110 degrees centigrade for an hour) and/or coated with the same to stabilize the braid matrix as described.

Figure 16:
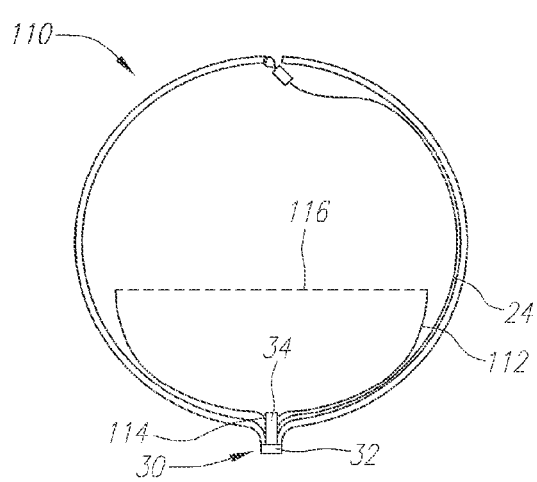

Implant 110 shown in FIG. 16 offers another yet another approach for improved embolizing (or flow disrupting) effect with little or no effect on crossing profile. Such effect is accomplished by affixing an innermost/third braid layer 112 to inner band 34 at its proximal end 114. It may be welded, glued, soldered or otherwise affixed thereto. The distal end of the braid 116 may be trimmed and formed as shown or otherwise. For example, the cup so-formed may closely follow the inner periphery of the device up to or past its equator.

As with variations in the previous figures, the third layer incorporated in the implant simply deploys and recaptures in unison with the rest of the implant. Unique, however, to the architecture of FIG. 16 is that the proximal end 114 of the braid is stably secured, but secured such that it does not require space in the hub (e.g., within the outer marker band 32) without dimensional stackup.

Figure 17:
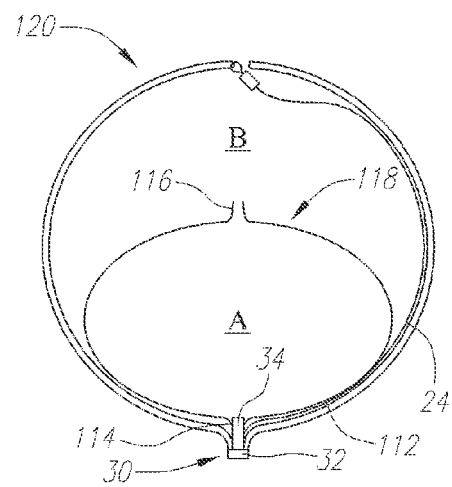

A related implant configuration is shown in FIG. 17. Here, in implant 120, the same proximal end 114 attachment approach is employed. Yet, instead of forming (e.g., by heatsetting) the inner layer of braid into a cup shape, an inner ball 118 is formed. The proximal side of the ball improves overall proximal-side implant density, and also defines separated flow stagnation zones A and B within the implant to further assist in thrombus formation within the implant.

Inner ball body 118 may be shape set over a form. Alternatively, and more advantageously, the shape can be formed without either an external or internal form by bunching the braid up and tying it onto a mandrel for heatsetting. Such a "free-forming" approach is functionally advantageous because it maximizes braid angle (hence, density) in the final body. Yet, any resulting inconsistency in shape is manageable given that the only outer body of the implant defined by braid layers 12 and 14 is in contact with an aneurysm.

Irrespective of how it is formed (and the particular braid configuration selection), the inner ball 118 within the architecture will be configured so that it will not interfere with the distal end of the implant body/shell and/or marker and tether when the device is compressed for delivery or recapture.

More generally, FIG. 18 provides an overview of implant-side of a treatment system 200. The system includes an implant 10 (90, 100, 110, 120) and a pusher sleeve or catheter shaft 210 ultimately attached to a handle 220 (e.g., as shown in FIGS. 19A-19-E). Any of these may be constructed according to the teachings herein and/or incorporated by reference.

One handle construction includes a single plunger. The plunger pulls a collar that progressively engages and pulls sockets connected to the wires; first each control wire 212 is pulled (one at a time), then the anchor wire 214. Such action is illustrated in FIGS. 19A-19E and 20A-20E. FIGS. 19A and 20A show the device components as removed from packaging. FIG. 19B illustrates unlocking the handle plunger 222 with a 120 degree rotation relative to handle body 224. Such action has no effect on the detachment interface 216 shown in FIG. 20B. However, progressive pull of the plunger in FIGS. 19C-19E effect the release of the system as shown in FIGS. 20C-20E.

Figure 21:
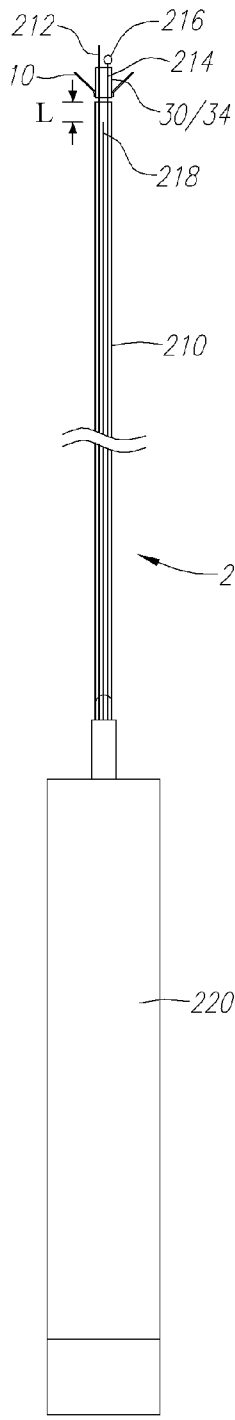
FIG. 21 shows an optional improvement to the architecture of the same system.

FIG. 21 shows an optional improvement to the architecture of system 200. Here, system 200' has only one "true" control wire 212 received within the hub or inner band 30/34 of the implant 10. Even so, the implant remains securely/stably attached to the catheter shaft by virtue of the control wire interaction with anchor ball 216 (e.g., as formed by laser or as otherwise configured).

Release of the implant is effected as if progressing from the steps in FIGS. 19C and 20C to 19E and 20E. However, a third (floating or actuated) "dummy" wire 218 is still loaded within the lumen of pusher shaft 210. Use of this wire maintains a close-packed arrangement of the wires inside shaft 210, which can be important in determining wire position within a tortuous setting. Yet, release angle may be increased and plunger pull force reduced because the wires within the implant have more space between them allowing for spatial accommodation.

Note that the length "L" by which wire 218 is inset within the pusher shaft may vary depending on purpose. It may have no inset (i.e., essentially abut the implant proximal end). It may be inset by about 1 mm so that any forward motion in a tortuous setting does not result in contact with the implant. Or it may be inset to a greater degree (e.g., between about 1 cm and 5 cm) to improve distal tip flexibility of delivery pusher shaft 210.

Figure 22A:
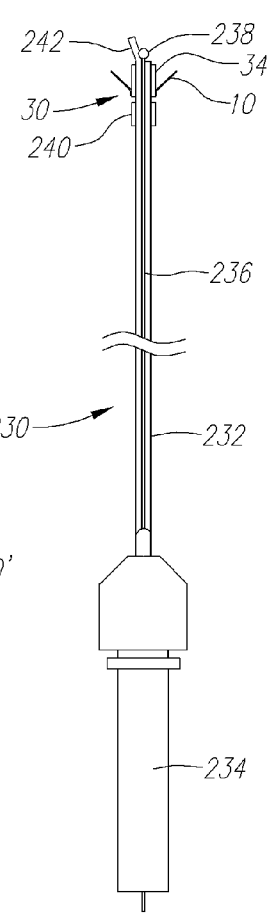
FIGS. 22A and 22B show an alternative delivery system interface engaged and disengaged, respectively.
Figure 22B:
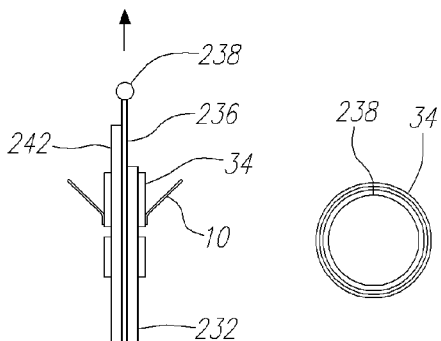

FIGS. 22A and 22B show an alternative delivery system interface in engaged and disengaged states, respectively. Here, system 230 comprises a catheter/pusher sleeve 232 actuated with the assistance of a typical torquer 234. Torquer 234 locks a position of a central wire 236 including an anchor ball for implant 10 delivery. A bumper or shoulder feature is provided by a band 240 that may be affixed to the catheter (optionally a Pt band also serving as a marker) to abut a hub 30 of the implant for pushing. Alternatively, a full-length pusher sheath 240' slidably received over sheath 232 may be provided for use as described below.

However configured (i.e., whether utilizing a terminal band 240, or full-length sheath 240' concentric with sleeve 232) engagement is achieved between the implant and pusher shaft 232 by virtue of extension 242 that is offset into an interfering relationship with an inner band 34 of the implant when the anchor ball 238 is in a retracted position as shown in FIG. 22A. When wire 236 (and its terminal ball feature 238) is advanced as shown in FIG. 22B, extension section 242 is free to move (e.g., to return to its original position by elastic action or upon catheter shaft withdrawal) and slide out of the implant. In an alternative mode of operation (e.g., in embodiments with a full length outer sleeve 240'), disengagement may be accomplished by withdrawing sleeve 232 to relieve locking interference without advancing the anchor wire 236 and ball 238.

Figure 23A:
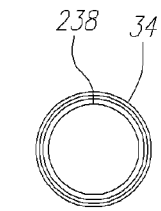
FIG. 23A shows an end-on view of the delivery system interface as pictured in FIG. 22B.

In any case, FIG. 23A is an end-on view of the delivery system interface as pictured in FIG. 22B. As shown, no interference between the ball 238 and/or extension persists once wire 236 is advanced and/or sleeve 232 withdrawn.

Figure 23B:
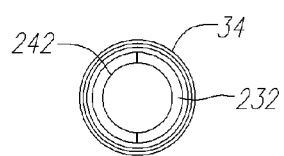
FIGS. 23B and 23C illustrate alternative end-on views of the configuration of a pusher shaft in the same system.
Figure 23C:
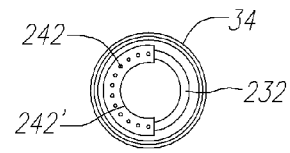

FIG. 23B portrays a similar view without the wire 236 and ball 238 in place. It shows extension 242 and catheter body 232. And while they are illustrated as formed in one manner (i.e., with a 90 degree cut-down), it is to be appreciated that the extension may instead be formed by an angular cut or otherwise. Indeed, FIG. 23C shows an approach in which the extension section is formed by pushing over the catheter wall on one side to meet the other and optionally heat setting, fusing or gluing the component parts 242 and 242' together. Still further, shaft 232 can be modified with cutout features along its length to provide flex performance advantages.

Figure 24A:
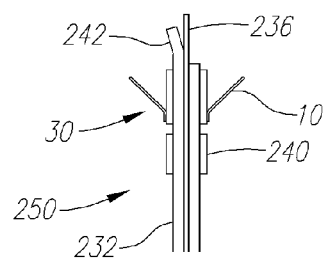
FIGS. 24A and 24B show alternative delivery system interface options (engaged and disengaged, respectively) based on the pusher shaft configuration in FIG. 23C.
Figure 24B:
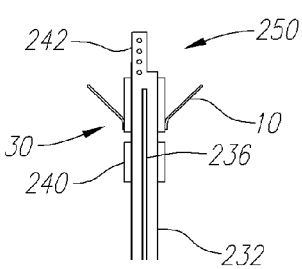

FIGS. 24A and 24B show an alternative delivery system interface 250 option (engaged and disengaged, respectively) based on the pusher shaft extension configuration in FIG. 23C. Due to the increased wall thickness offered by the double wall layer, the system can work much as that shown in FIGS. 22A and 22B, except without need for a separated distal interference feature (such as a anchor ball/band). As such, withdrawal of wire 236 will relieve the interference and unlock the pusher sleeve 232 (specifically, the associated extension) for withdrawal from the implant 10.

Figure 25:
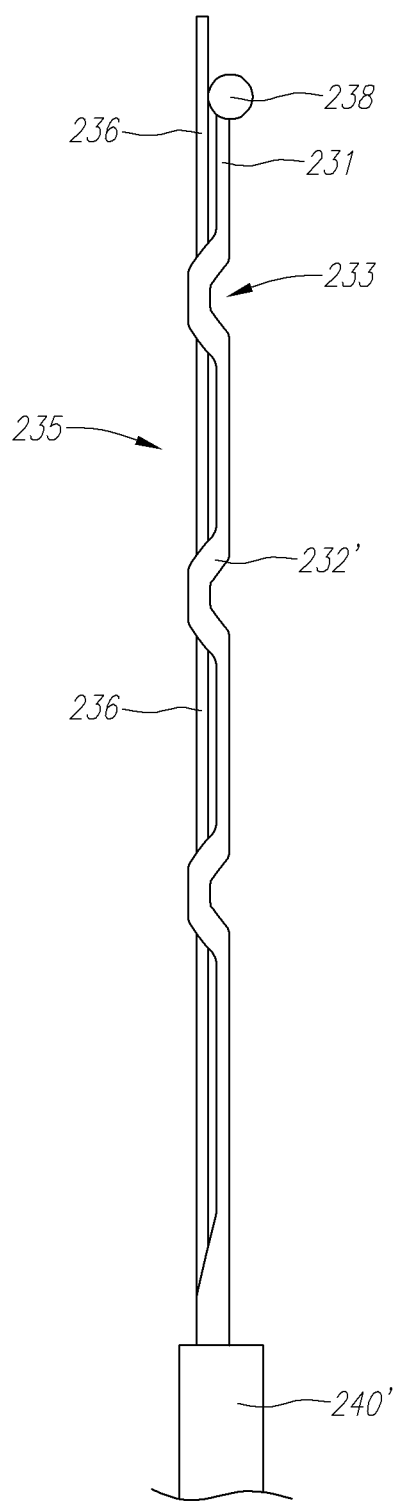
FIG. 25 shows a partial assembly view of an embodiment related to that in FIGS. 24A and 24B.

FIG. 25 is partial assembly view of a related embodiment in which a sleeve 232' serves as the base or foundation for the anchor ball 238. Such a ball may be formed at the end of the sleeve in a number of ways. One approach employs a metal hypotube (e.g., stainless steel, CoCr or Nitinol) that is etched or laser cut to define an elongate "wire" extension 231. Then, utilizing laser energy, the ball is formed at the end of wire. Alternatively, a cylindrical band may be affixed thereto by welding, etc.

In addition, a cutout pattern 235 is advantageously made in the hypotube sleeve to improve flex performance. The cutouts 233 alternate and/or spiral on either side of control wire. As is known, such patterning can provide for unbiased flex. Kerf width may be between about 0.002 and about 0.010 inches. When employing larger (e.g., about 0.5 to about 3 mm as illustrated in FIG. 25) kerfs/cutouts such an approach maintains alignment of the control wire in a central location.

As shown, a core member 236 is received concentrically within sleeve 232' and the sleeve concentrically within an outer catheter/pusher sheath 240'. The outer sheath may serve to encapsulate the flex-tuned sleeve and bear a hydrophilic coating for lubricity. Moreover, the sheath member may incorporate a terminal marker band.

Figure 26:
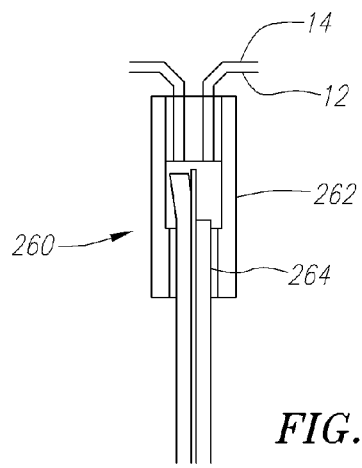
FIG. 26 shows an alternative implant-side interface with a delivery system as presented in FIGS. 24A and 24B.

FIG. 26 shows an alternative implant-side interface with a delivery system as presented in FIGS. 24A and 24B. Here an implant socket 260 is provided. Socket 260 may be defined by a cup 262 attached to one or more implant braid layers (12/14), by welding or otherwise, and a reducer tube 264 threaded, pressed or otherwise affixed in the proximal end of the cup. Note that with such an arrangement that implant pushing can be accomplished without a shoulder 240 or other proximal interface like an overlying shaft 210 or sheath 240' configured to abut a proximal end of the implant.

Instead, both push and pull (for withdrawal) force application can occur within the socket chamber. While such a socket will typically be larger than the previous interfaces shown, it is easily retrofit or used as and alternative to the screw-type release approaches employed in many vessel sacrifice and closure devices as sold by AGA Medical, Inc. and others.

Figure 27A:
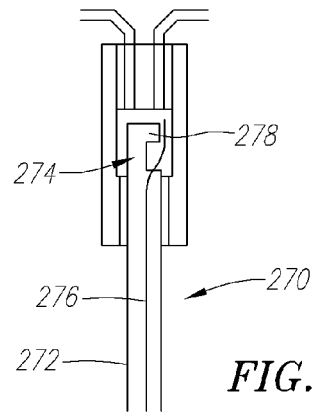
FIGS. 27A, 27B, and 27C show an implant-side interface like that presented in FIG. 26 with an alternative pusher-side architecture, along with a detail view illustrating improvements thereto.
Figure 27B:
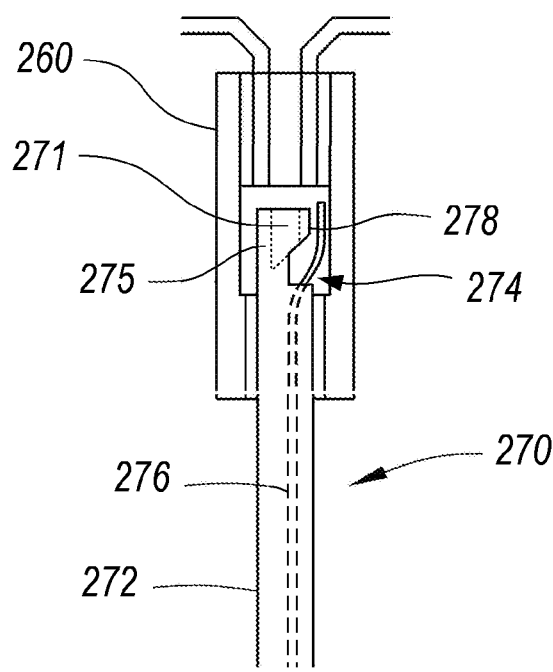
Figure 27C:
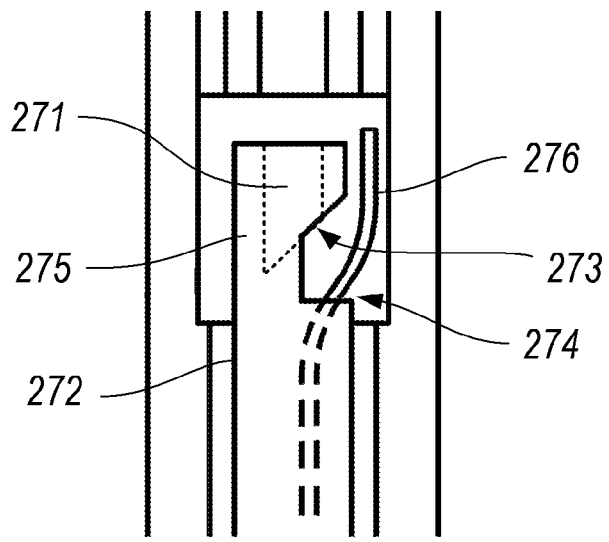

The delivery system configuration in FIGS. 27A-C shows the same implant-side interface 260, with an alternative pusher-side engagement/disengagement (or latch) architecture 270. This architecture is a simplified version of that shown in FIG. 18 of Becking, et al. referenced above. Specifically, a pusher shaft sleeve 272 (e.g., metal hypotube) is provided with a single window cutout 274. The window (configured as a square cutout, rounded, or a simple kerf) operates as a side port allowing a core member 276 (e.g., NiTi ribbon) to pass therethrough and provide interference against pusher shaft distal end at face 278 to prevent delivery system detachment until core member withdrawal.

This delivery system architecture (whether adapted as described in the referenced application, with the implant size socket approach, or otherwise) may, however, be improved as illustrated in the detail view at right in FIG. 27A-C. Here, a distal portion of the cutout is sized and angled to ease the transition of core member 276 out of the inner lumen of sleeve 272. In addition, an insert 271 may be included in the distal end of the sleeve to back or support the control wire (or ribbon lying flat against the insert) when engaged in an interference fit within an implant. The angulation of overhanging portion 273 and backing of insert 271, especially together, can reduce point stress on the detachment interface and ease control member withdrawal resulting in advantageously lower detachment actuation force(s). The overhang portion 273 may define a surface that is transverse to or oblique relative to a central axis of the sleeve 272 or another central a longitudinal axis of the system. The surface of the overhang portion 273 may be defined by the distal section 278 of the sleeve 272 or by an insert 271. The overhang portion 273 may deflect the core member 276 when the core member 276 is provided with a distally directed force against the overhang portion 273 and/or the surface defined thereby. Likewise, it may enable utilizing lower strength material for the control member such as polymers that can offer improved flex performance as well as lubricity. For production, a cylindrical insert 271 may be press fit welded, etc. in a distal section 275 of the sleeve 272 hypotube, and then be machined together to obtain matched surfaces. Alternatively, the distal section of the sleeve 272 may be formed of a solid material that omits the inner lumen along the length of the distal section distal to the window 274.

A method of assembling a delivery system is disclosed. The method may include inserting a distal section of an elongate sleeve 272 into a socket 260 of an implant. A distal portion of a core member 276 is advanced through the sleeve 272. The distal portion of the core member 276 is then passed through a window 274 of the sleeve 272. The distal portion of the core member 276 is engaged into an interference fit with the distal section of the sleeve 272 within the socket 260 of the implant.

Figure 28A:
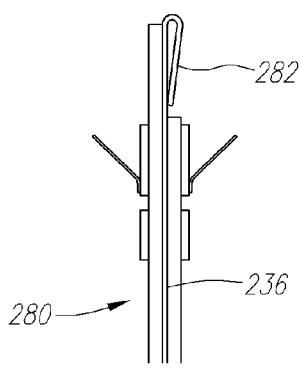
FIGS. 28A and 28B shows an alternative engagement/disengagement interface for a system like that shown in FIGS. 22A and 22B.
Figure 28B:
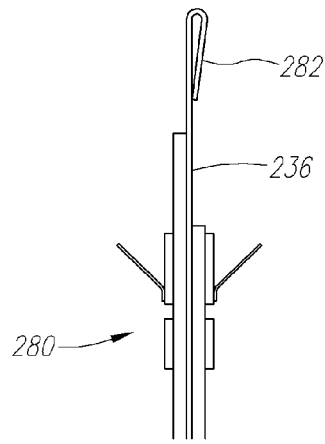
Figure 29:
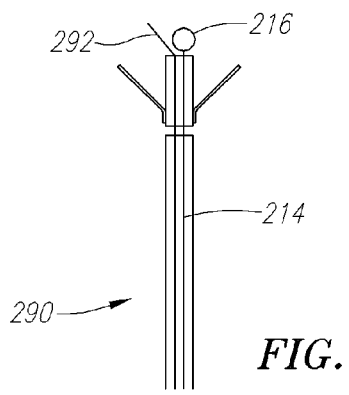
FIGS. 29 and 30 shows yet another engagement/disengagement architecture for each of a braid-type implant and embolic coil, respectively.

FIGS. 28A and 28B show a further alternative latch interface 280 for a system like that shown in FIGS. 22A and 22B. In this system, a bent back wire "Sheppard's" hook 282 serves the function of the ball in the former system. Such a system offers the advantage of very low cost production, as well as a secure anchoring feature. FIG. 29 shows a system 290 most closely related to that in FIG. 21, except that multiple control and/or dummy wires are replaced with a single ribbon 292.

Figure 30:
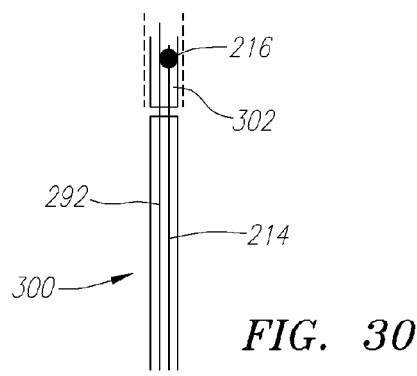

Finally, FIG. 30 shows a detachment system 300. As in system 290 a ribbon 292 may be used in conjunction with a round anchor wire 214 with a ball-shaped anchor 216. An alternative approach that may be used in either system is to employ a ribbon as the "anchor wire" and form the interference feature at its end by tying a knot therein (as a substitute for a laser-formed ball). Such a knot can be shape set, glued or welded to stabilize its shape. It can be reliably be produced at low cost at a very small size, on a ribbon. A socket-type interface can be formed within the coil by fitting a collar feature 302 within its proximal end. The collar may be threaded-in (i.e., into the coils like a thread pitch). An alternative approach involves flowing solder between the coils and defining a lumen therein using a removable mandrel. The mandrel may be prepared in any manner to facilitate its removal, including those described for the removable hub in connection with the improvement described in connection with FIG. 9B.

In the various delivery system architectures, the catheter/pusher shaft may comprise a simple extrusion (e.g., PI, PET, PTFE, FEP, PEEK, etc.) or may be constructed using conventional catheter construction techniques and include a liner, braid support and outer jacket (not shown). An exemplary construction is available through MicroLumen, Inc. as Braid Reinforced Polyimide. A distal section of the Polyimide may be ablated and replaced with fused Pebax to provide a softer or progressively-flexible end to the catheter. A loading sheath is typically provided over the pusher shaft. Advantageously, the loading sheath is splittable.

If not preloaded, after removal from sterile packaging (not shown), the implant is pulled into the loading sheath. The loading sheath is received within the hub of the catheter to be used for implant delivery and the implant is advanced into the catheter. Then, the implant may be advanced to and deployed at a treatment site. Or it may be retrieved in exchange for another size implant or repositioned, if desired, prior to ultimate detachment as illustrated in the incorporated patent application subject matter.

In the present invention, the subject methods may include each of the physician activities associated with implant positioning and release. As such, methodology implicit to the positioning and deployment of an implant device forms part of the invention. Such methodology may include placing an implant within a brain aneurysm, or at parent vessel targeted for occlusion, or other applications. In some methods, the various acts of implant introduction to an aneurysm or parent vessel are considered.

More particularly, a number of methods according to the present invention involve the manner in which the delivery system operates in reaching a treatment site, for example. Other methods concern the manner in which the system is prepared for delivering an implant, for example attaching the braid ball to the delivery system. Any method herein may be carried out in any order of the recited events which is logically possible, as well as in the recited order of events, or slight modifications of those events or the event order.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. An implant for occluding a target area of a patient's vasculature, comprising:
    a shell comprising globular inner and outer braid layers that define a plurality of openings, the inner and outer braid layers and openings collectively defining a shell porosity, the shell comprising a distal region and a proximal region, the shell being expandable from a compressed configuration to an expanded configuration;
    a proximal hub component coupled to the proximal region of the shell thereby gathering and securing the inner and outer braid layers of the proximal region; and
    an intermediate braid layer, interposed between the inner and outer braid layers, coupled to the shell along at least the proximal region thereof, the intermediate braid layer comprising a plurality of pores extending therethrough,
    wherein the shell and the intermediate braid layer provide a combined porosity less than the shell porosity such that blood flow into the implant is more restricted along the proximal region than along the distal region of the shell,
    wherein the intermediate braid layer has a proximal end that is not secured within the proximal hub and a distal end that terminates at a position proximal to a distal end of the shell.

2. The implant of claim 1, wherein the intermediate braid layer terminates at a longitudinal midsection of the shell.

3. The implant of claim 1, wherein the intermediate braid layer comprises a proximal end portion, the proximal end portion being positioned distal to the proximal hub component.

4. The implant of claim 3, wherein the intermediate braid layer proximal end portion is not secured to the proximal hub component.

5. The implant of claim 1, wherein the intermediate braid layer comprises a band of braided material.

6. The implant of claim 1, wherein the intermediate braid layer comprises a polymer coating or a hydrogel coating.

7. The implant of claim 1, wherein the intermediate braid layer extends around the proximal region of the shell configured to be positioned near a neck of an aneurysm.

8. The implant of claim 1, wherein the distal region comprises a flattened top.

9. An implant for occluding a target area of a patient's vasculature, the implant comprising a shell comprising globular first and second braid layers, a hub, and a braided band interposed between the first and second braid layers, the hub being coupled to an end portion of the implant thereby gathering and securing the first and second braid layers thereat, the braided band extending about a circumference of the implant and positioned in a space between the hub and a longitudinal midsection of the shell, the braided band decreasing a porosity of the implant, the shell being expandable from a compressed configuration to an expanded configuration, wherein the braided band has a proximal end that is not secured within the hub and a distal end that terminates at a position proximal to a distal end of the shell.

10. The implant of claim 9, wherein a proximal end portion of the braided band is not secured to the hub.

11. The implant of claim 9, wherein the braided band comprises a polymer coating or a hydrogel coating.

12. The implant of claim 9, wherein the braided band extends from a position distal to the hub and terminates at a longitudinal midsection of the implant.

13. The implant of claim 9, wherein a distal region, opposite the hub, comprises a flattened top.

* * * * *